US007183523B2

(12) United States Patent
Lu

(10) Patent No.: US 7,183,523 B2
(45) Date of Patent: Feb. 27, 2007

(54) WRIST REST EQUIPPED WITH A HEATING DEVICE

(76) Inventor: Chiang-Tsun Lu, No. 12, Lane 191, Sec. 1, Jhangshuei Rd., Sioushuei Hsiang, Changhua Hsien (TW)

(*) Notice: Subject to any disclaimer, the term of this patent is extended or adjusted under 35 U.S.C. 154(b) by 0 days.

(21) Appl. No.: 11/269,639

(22) Filed: Nov. 9, 2005

(65) Prior Publication Data

US 2006/0273079 A1 Dec. 7, 2006

(30) Foreign Application Priority Data

Jun. 1, 2005 (TW) ............................. 94209104 U

(51) Int. Cl.
*H05B 3/06* (2006.01)
*A61N 1/39* (2006.01)
(52) U.S. Cl. ........................................ 219/521; 607/99
(58) Field of Classification Search ................ 219/521, 219/458, 507, 509, 510, 515, 520, 200, 201; 338/226; 607/96, 99
See application file for complete search history.

(56) References Cited

U.S. PATENT DOCUMENTS

| | | | | | |
|---|---|---|---|---|---|
| 2,148,742 | A | * | 2/1939 | Graham | ...................... 392/445 |
| 4,145,602 | A | * | 3/1979 | Lee | ............................ 392/382 |
| 4,916,280 | A | * | 4/1990 | Havette | ...................... 219/731 |
| 5,593,610 | A | * | 1/1997 | Minerich et al. | ........... 219/728 |
| 6,133,556 | A | * | 10/2000 | Ramsey et al. | ............. 219/521 |
| 6,431,360 | B1 | * | 8/2002 | Julius | ........................ 206/494 |

* cited by examiner

*Primary Examiner*—Daniel Robinson
(74) *Attorney, Agent, or Firm*—Lowe Hauptman & Berner, LLP

(57) ABSTRACT

A wrist rest equipped with a heating device has a base, a heating device and a cushion. The base has a recess and a chamber. The heating device is mounted in and on the base and has a controller, a heating element, a switch and a power source. The controller is mounted in the chamber and controls operation of the heating device. The heating element is mounted in the recess and connected electrically to the controller. The switch is connected electrically to the controller to turn the heating element on and off. The power source is connected electrically to the controller to supply electricity to the heating device. The cushion is mounted in the recess above the heating element and is heated by heat from the heating element to improve the blood circulation in the mouse user's wrist area while a user operates the computer mouse.

11 Claims, 4 Drawing Sheets

WRIST REST EQUIPPED WITH A HEATING DEVICE

BACKGROUND OF THE INVENTION

1. Field of the Invention

The present invention relates to a wrist rest, and more particularly to a wrist rest equipped with a heating device.

2. Description of Related Art

A conventional mouse pad combined with a gel-filled wrist rest comprises a plastic bottom and a surface covered with cloth.

A user supporting his or her wrist on the conventional mouse pad for a long time while operating a computer mouse may interfere with circulation of blood in the wrist accompanied by fatigue, numbness and aching and then develop musculoskeletal damage such as Repetitive Strain Injury (RSI) and Carpal Tunnel Syndrome (CTS).

To overcome the shortcomings, the present invention provides a wrist rest equipped with a heating device to obviate or mitigate the aforementioned problems.

SUMMARY OF THE INVENTION

The main objective of the present invention is to provide a wrist rest equipped with a heating device that can increase the circulation of blood and relieve taut tendons and muscles in the wrist area and lower ailments associated with overuse of computer such as RSI and CTS.

To accomplish the foregoing objective, the wrist rest has a base, a heating device and a cushion. The base has a top, a bottom, a sidewall, a recess, a chamber and a cover. The recess is defined in the top of the base, and the chamber is defined in the bottom of the base. The cover is mounted detachedly on the bottom of the base to close the chamber. The heating device is mounted in and on the base and comprises a controller, a heating element, a switch and a power source. The controller is mounted in the chamber and controls operation of the heating device. The heating element is mounted in the recess and connected electrically to the controller. The switch is mounted in the sidewall of the base and connected electrically to the controller to turn the heating element on and off. The power source is connected electrically to the controller to supply electricity to the heating device and comprises at least one battery and an external power input terminal. The cushion is oval, is a contoured resilient pad and is mounted in the recess above the heating element. The cushion is heated by heat from the heating element to improve the blood circulation in the mouse user's wrist area.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
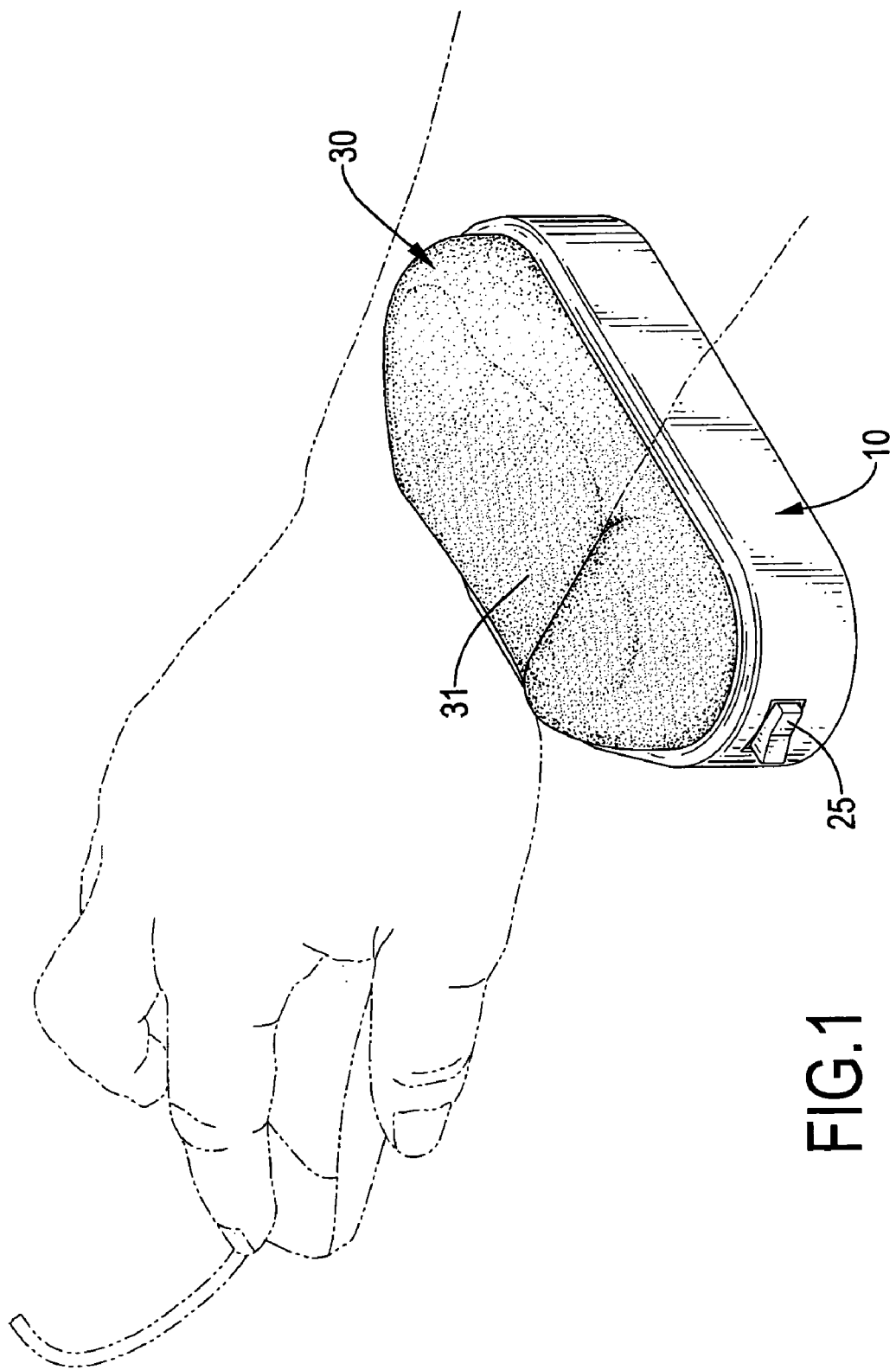
FIG. 1 is an operational perspective view of a wrist rest in accordance with the present invention.
Figure 2:
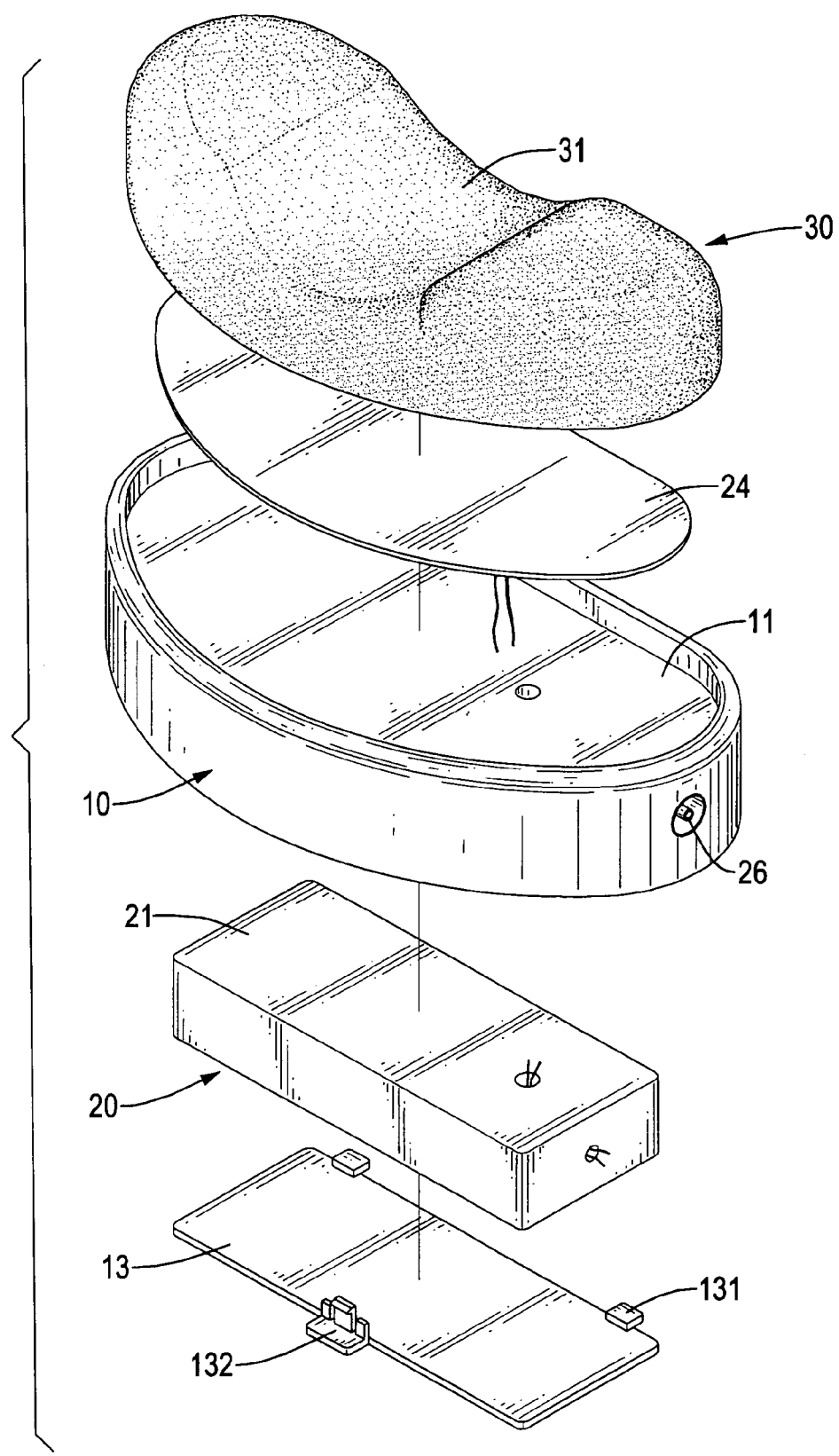
FIG. 2 is an exploded perspective view of the wrist rest in FIG. 1.
Figure 3:
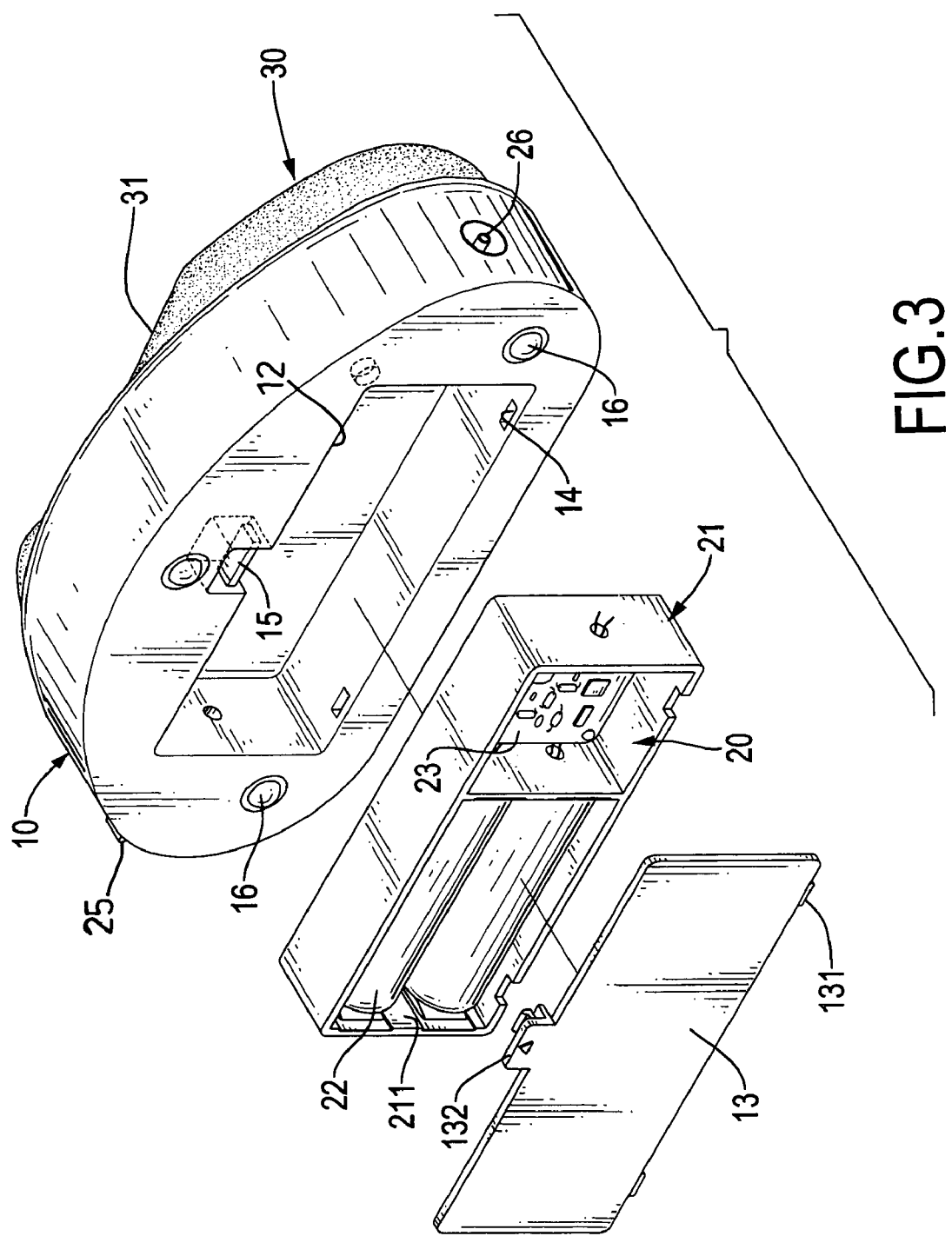
FIG. 3 is a partially exploded bottom perspective view of the wrist rest in FIG. 1.

With reference to FIGS. 1, 2 and 3, a wrist rest in accordance with the present invention comprises a base (10), a heating device (20) and a cushion (30).

The base (10) is oval, is made of plastic, has a top, a bottom, a sidewall, a recess (11), a chamber (12) and a cover (13) and may have at least three sliding feet (16).

The recess (11) is formed in the top of the base (10).

The chamber (12) is formed in the bottom of the base (10) and has a front sidewall, a rear sidewall, two optional notches (14) and an optional hook (15). The notches (14) are formed in the rear sidewall, and the hook (15) is formed in the front sidewall.

The cover (13) is mounted detachedly on the bottom of the base (10) to close the chamber (12) and has a front edge, a rear edge, two optional tabs (131) and an optional latch (132). The tabs (131) are formed on and protrude out from the rear edge of the cover (13) and correspond to and are mounted respectively in the notches (14) in the chamber (12). The latch (132) is formed on and protrudes out from the front edge of the cover (13) and corresponds to and engages the hook (15) in the chamber (12) to hold the cover (13) securely over the chamber (12).

The sliding feet (16) are defined in and protrude from the bottom of the base (10) to allow the wrist rest to slide smoothly on a desk surface.

Figure 4:
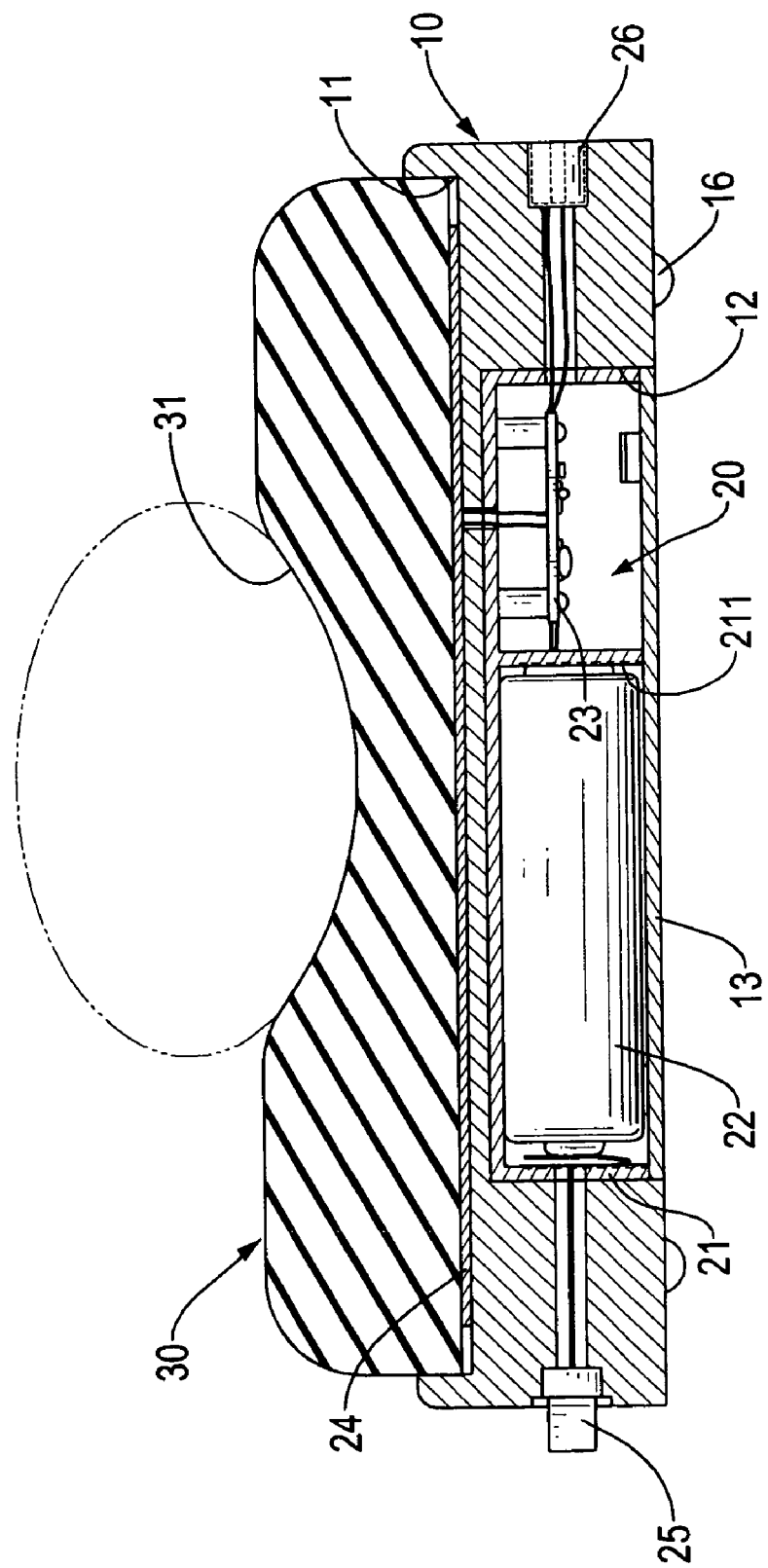
FIG. 4 is an enlarged rear view in partial section of the wrist rest in FIG. 1.

With further reference to FIG. 4, the heating device (20) is mounted in and on the base (10) and comprises an optional housing (21), a controller (23), a heating element (24), a switch (25) and a power source.

The housing (21) is mounted in the chamber (12) and may be partitioned into a battery compartment (211) and a controller compartment.

The controller (23) is mounted in the chamber (12), optionally in the housing (21) and the controller compartment of the housing (21) when the housing (21) is partitioned and controls operation of the heating device (20).

The heating element (24) is mounted in the recess (11) and is connected electrically to the controller (23).

The switch (25) is mounted in the sidewall of the base (10), is connected electrically to the controller (23) and turns the heating element (24) on and off.

The power source is connected electrically to the controller (23) to supply electricity to the heating device (20) and may be implemented with at least one battery (22), an external power input terminal (26) or both. The at least one battery (22) is mounted in the chamber (12), the housing (21) when the housing (21) is mounted in the chamber (12) or in the battery compartment (211) when the housing (21) is partitioned and is connected electrically to the controller (23). The external power input terminal (26) is mounted in the sidewall of the base (10), is connected to the controller (23) and connects to an external power source.

The cushion (30) is an oval contoured resilient pad, is mounted in the recess (11) above the heating element (24) and having a top surface and an optional saddle (31). The saddle (31) is defined in the top surface of the cushion (30) and formed to conform to a use's wrist.

In operation, when the switch (25) is powered on, the heating device (20) will be actuated to heat the heating element (24). The heat generated by the heating element (24) will keep the cushion (30) in proper temperature, so that the blood circulation in the mouse user's wrist area is improved to comfort the user's wrist.

Even though numerous characteristics and advantages of the present invention have been set forth in the foregoing description together with details of the structure and function of the invention, the disclosure is illustrative only.

Changes may be made in detail especially in matters of shape, size, and arrangement of parts within the principles of the invention to the full extent indicated by the broad general meaning of the terms in which the appended claims are expressed.

What is claimed is:

1. A wrist rest equipped with a heating device comprising:
   a base being oval, made of plastic and having
      a top;
      a bottom;
      a sidewall;
      a recess formed in the top of the base;
      a chamber formed in the bottom of the base and having
         a front sidewall; and
         a rear sidewall; and
      a cover mounted detachedly on the bottom of the base to close the chamber and having
         a front edge; and
         a rear edge;
   a heating device mounted in the base and comprising
      a controller mounted in the chamber;
      a heating element mounted in the recess and connected electrically to the controller;
      a switch mounted in the sidewall of the base and connected electrically to the controller to turn the heating element on and off; and
      a power source connected electrically to the controller to supply electricity to the heating device;
   a cushion being an oval contoured resilient pad, mounted in the recess of the base above the heating element and having a top surface.

2. The wrist rest equipped with a heating device as claimed in claim 1, wherein the base further comprises at least three sliding feet defined in and protruding from the bottom of the base to allow the wrist rest to slide smoothly on a desk surface.

3. The wrist rest equipped with a heating device as claimed in claim 2, wherein the power source is at least one battery mounted in the chamber.

4. The wrist rest equipped with a heating device as claimed in claim 2, wherein the power source is
   a power input terminal mounted in the sidewall of the base, connected to the controller and connecting to an external power source; and
   at least one battery mounted in the chamber.

5. The wrist rest equipped with a heating device as claimed in claim 3, wherein the heating device further comprises a housing mounted in the chamber, and the battery and the controller are mounted in the housing.

6. The wrist rest equipped with a heating device as claimed in claim 5, wherein
   the housing is partitioned into a battery compartment and a controller compartment;
   the battery is mounted in the battery compartment;
   the controller is mounted in controller compartment.

7. The wrist rest equipped with a heating device as claimed in claim 4, wherein
   the heating device further comprises a housing mounted in the chamber; and
   the battery and the controller are mounted in the housing.

8. The wrist rest equipped with a heating device as claimed in claim 7, wherein
   the housing is partitioned into a battery compartment and a controller compartment;
   the battery is mounted in the battery compartment; and
   the controller is mounted in controller compartment.

9. The wrist rest equipped with a heating device as claimed in claim 8, wherein the cover further comprises a saddle defined in the top surface of the cushion and formed to conform to a use's wrist.

10. The wrist rest equipped with a heating device as claimed in claim 9, wherein
    the chamber further has
       two notches formed in the rear sidewall; and
       a hook formed in the front sidewall; and
    the cover further has
       two tabs formed on and protruding out from the rear edge of the cover and corresponding to and are mounted respectively in the notches in the chamber; and
       a latch formed on and protruding out from the front edge of the cover and corresponding to and engaging the hook in the chamber to hold the cover securely over the chamber.

11. The wrist rest equipped with a heating device as claimed in claim 1, wherein the cover further comprises a saddle defined in the top surface of the cushion and formed to conform to a use's wrist.

* * * * *